United States Patent [19]
Millman

[11] Patent Number: 5,653,701
[45] Date of Patent: Aug. 5, 1997

[54] OSTOMY SUPPORT BELT

[75] Inventor: Leonard V. Millman, Las Vegas, Nev.

[73] Assignee: Desert Shield Trust, Las Vegas, Nev.

[21] Appl. No.: 552,036

[22] Filed: Nov. 2, 1995

Related U.S. Application Data

[60] Continuation-in-part of provisional application No. 60/000,148, Jun. 12, 1995.

[51] Int. Cl.⁶ .................................................. A61F 5/44
[52] U.S. Cl. ............................................ 604/345; 604/337
[58] Field of Search .................................. 604/332, 337, 604/345, 343, 350, 340, 338, 339

[56] References Cited

U.S. PATENT DOCUMENTS

| | | | |
|---|---|---|---|
| 2,205,270 | 6/1940 | Perry | 604/337 |
| 4,973,323 | 11/1990 | Kaczmarek et al. | 604/337 |
| 5,026,362 | 6/1991 | Willett | 604/332 |
| 5,135,519 | 8/1992 | Helmer | 604/332 |
| 5,248,308 | 9/1993 | Von Emster | 604/332 |

FOREIGN PATENT DOCUMENTS 2722445  11/1978  Germany .................. 604/345

OTHER PUBLICATIONS

Translation of German Patent No. 27 22 445 Nov. 23, 1978.

*Primary Examiner*—John G. Weiss
*Assistant Examiner*—Ki Yong O
*Attorney, Agent, or Firm*—Foster & Foster

[57] ABSTRACT

An ostomy support belt includes a main pocket for supporting the weight of a conventional pouch for holding bodily drainages. A secondary pocket is provided on the inside of the ostomy support belt in which a support plate is inserted for providing additional lateral support to the areas of the skin and abdomen surrounding the stoma and to increase adhesion where the pouch attaches to the skin surrounding the stoma and to prevent leakage, skin irritation, mounding, and herniation. A guard may be attached to the outside of the belt at a location corresponding to the stoma to prevent the stoma from damage due to external forces.

16 Claims, 6 Drawing Sheets

OSTOMY SUPPORT BELT

RELATED APPLICATION

This is a continuation-in-part of provisional U.S. patent application Ser. No. 60/000,148, filed 12 Jun. 1995.

TECHNICAL FIELD

The present invention relates to appliances used by ostomates, and more particularly to ostomy support belts.

BACKGROUND OF THE INVENTION

Ostomates have always faced numerous difficulties with respect to their medical conditions. The numerous difficulties are presented in handling drainages that exit from the body through a stoma surgically provided to the ostomate, typically in the abdominal region. Attempts are continually being made to improve ostomy appliances and remedy the various difficulties faced by ostomates.

A primary problem faced by ostomates is that of undesired leakage around the containment appliance attached to the stoma location. Typically, a pouch for containing and holding the bodily drainages (i.e., human excrement, such as fecal matter or urine) is adhesively attached to the skin surrounding the stoma. Any type of relative movement between the surrounding skin area and the adhesive material will create a channel or a track through which bodily drainages will leak. Such leakages are the source of humiliation and embarrassment for the ostomate, not to mention the other problems associated with smell and damage to clothing. Thus, although many ostomates desire to enjoy an active lifestyle, the problems associated with leakage have such a tremendous downside that most ostomates have traditionally been relegated to a sedentary lifestyle.

Another problem faced by ostomates relates to irritation of the skin surrounding the stoma. A primary cause of skin irritation is the downward pulling force the pouch places on the skin surrounding the stoma as the pouch fills with human elimination. As discussed above, this pulling force may also cause leaks to occur between the adhesive material and the skin, which may cause skin irritation.

Still another common problem faced by ostomates is the mounding up of the skin and tissue surrounding the stoma. Although perhaps some mounding is inevitable from the stoma itself, such mounding is exacerbated when the skin and tissue are required to support the weight of the pouch containing bodily elimination.

Yet another problem that ostomates must confront relates to herniation. The stoma itself is a temporary or permanent opening typically created in the abdominal wall through surgery. Thus, once healing has occurred, the stoma usually protrudes through the skin and abdominal wall. Nevertheless, herniation is often caused by compromising the integrity of the abdomen due to surgery to create the stoma, combined with the weight of the pouch pulling the adhesive area of the pouch on the skin of the abdomen.

Another concern of ostomates is to protect the stoma from trauma resulting from external contact, which can result from an active lifestyle (e.g. sports, dancing, etc.). In addition, the stoma can become irritated from continuous and repetitious outside contact by clothing worn by the ostomate, or things such as seat belts in vehicles or airplanes. The stoma is highly sensitive and capable of being irritated or damaged by even a small amount of external contact.

In view of the foregoing, a significant need exists to provide an ostomy support belt that will minimize the risk of bodily drainages leaking around the seal between the pouch for holding the elimination and the areas of skin to which the pouch attaches, that will support the substantial weight of the pouch as it fills with bodily drainages to avoid skin irritation, herniation, and mounding of the skin and tissue surrounding the stoma, and to protect the stoma from irritation and trauma associated with external contact.

SUMMARY AND OBJECTS OF THE INVENTION

It is a primary object of the invention to provide an ostomy support belt that supports the substantial weight of the pouch attached to the skin area surrounding the stoma of an ostomate.

Another object of the invention is to provide an ostomy support belt that is capable of holding the pouch in a discreet and tightly secured manner close to the ostomate's abdomen.

Another object of the invention is to provide an ostomy support belt that reduces the tendency of the skin and tissue at the areas surrounding the stoma to mound.

Yet another object of the invention is to provide an ostomy support belt that reduces risk of additional herniation in the abdomen at areas surrounding the stoma.

Still another object of the invention is to provide an ostomy support belt that will provide additional lateral support to the skin and tissue surrounding the stoma.

Another object is to provide an ostomy support belt that will aid adhesion of the pouch to the skin surrounding the stoma.

Another object is to reduce or totally eliminate leakage of the contents of the pouch.

Yet another advantage of the present invention is to provide an ostomy support belt that reduces skin irritation.

Another object of the invention is to provide an ostomy support belt that eliminates any pendulum effect that may otherwise be created by the pouch.

The foregoing objects are achieved by an ostomy support belt for use by all ostomates (i.e., persons with colostomies, ileostomies, or urostomies). An aperture is formed at a base location of the ostomy support belt so the belt can be placed with the aperture surrounding the stoma of an ostomate. A conventional pouch for receiving and holding bodily drainages is attached to the skin area surrounding the stoma. The belt includes a main pocket attached to the lower edge of the support belt for receiving and supporting the substantial weight of the pouch. The ostomy support belt further includes a secondary pocket formed on the inside of the belt corresponding to base location of the belt to be positioned in front of the area surrounding the stoma. A support plate is inserted into the secondary pocket. The support plate includes a support plate aperture sized to circumscribe the stoma to provide lateral support to the skin and tissue surrounding the stoma. A guard may be attached to the front side of the belt such that the guard extends over and protects the stoma from irritation or blunt trauma resulting from external contact.

Other objects, features, and advantages of the invention will become apparent from the following detailed description of the invention with reference to the accompanying drawings.

BRIEF DESCRIPTION OF THE DRAWINGS

Preferred embodiments of the invention are described below with reference to the accompanying drawings.

DETAILED DESCRIPTION OF THE INVENTION

Figure 1:
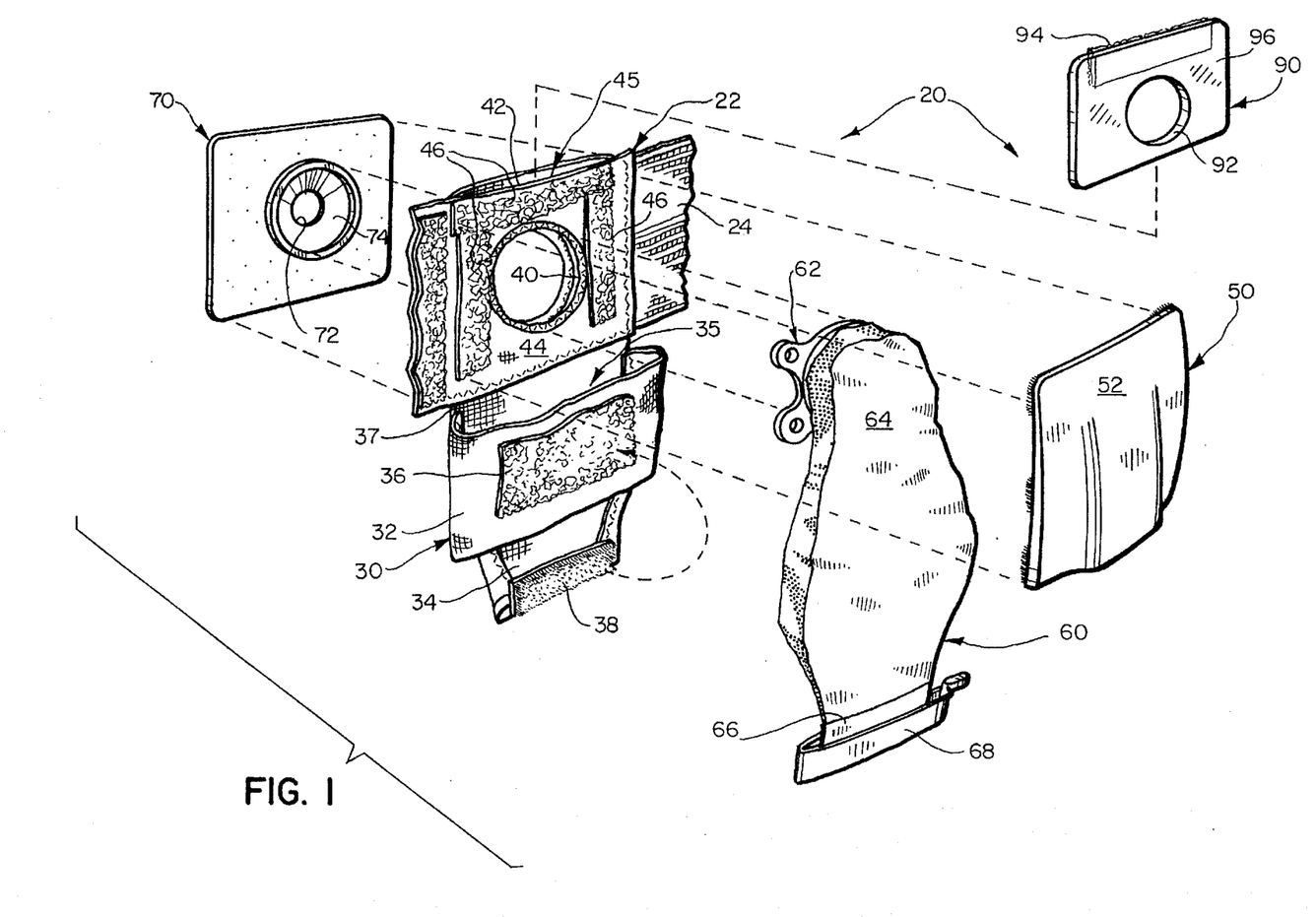
FIG. 1 is an exploded perspective view, partly in section, of an ostomy support belt according to the present invention.
Figure 2:
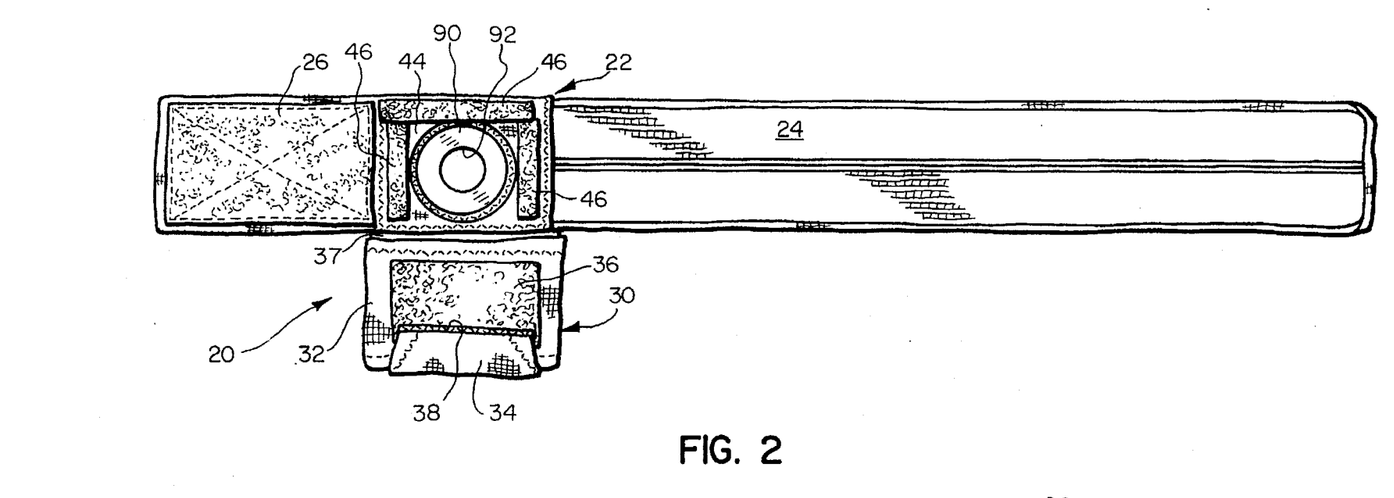
FIG. 2 is a front elevation view of the ostomy support belt of FIG. 1.
Figure 3:
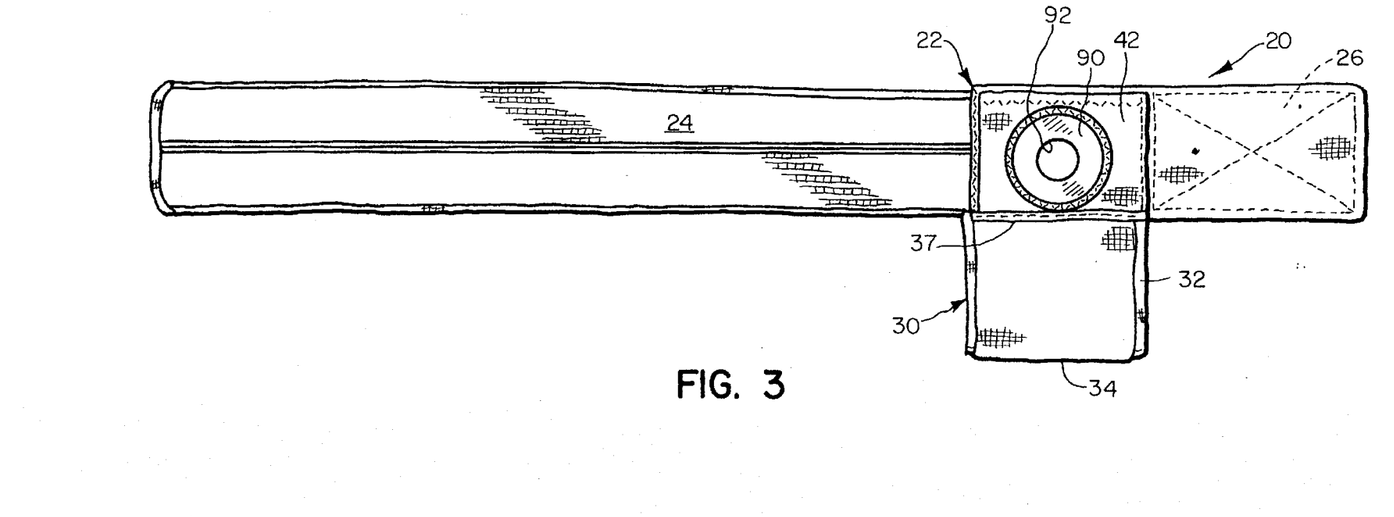
FIG. 3 is a rear elevation view of the ostomy support belt of FIG. 1.

FIG. 1 shows an ostomy support belt 20 comprising a base location 22 and a belt 24 for extending around an ostomate's waist. Any suitable belt may be used in conjunction with the present invention. One preferable belt is marketed by Nu-Hope Laboratories, Inc. of Pacoima, Calif. This belt combines two panels, elastic in nature, in a side-by-side relationship to provide ample structural support for the other components of the ostomy support belt. The base location is the main area to which the various components of the ostomy support belt of the present invention are secured. The belt includes an end segment 26 which has a fastener material, such as Velcro™, for quick placement and adjustability.

The belt further includes a first or main pocket 30 which is attached to the lower edge of the belt at the base location 22. The main pocket 30 provides a location for holding and supporting the weight of a conventional pouch (described below) which contains the ostomate's bodily drainages. The main pocket 30 comprises a main pocket panel 32 which forms the surrounding walls of the pocket, a lower flap 34 which forms the bottom wall of the pocket, and an upper extension portion 37 which hingedly attaches the main pocket to the base location 22 of the ostomy support belt. The main pocket articulates about the upper extension portion 37 (FIG. 4) to place the main pocket in a hide-away position. As shown in FIG. 1, the main pocket 30 provides an opening 35 into which a conventional containment pouch 60 (described in greater detail below) can be inserted. The main pocket 30 is intended to support the substantial weight of the pouch as it fills with bodily drainages via the stoma.

The size of the first or main pocket 30 is adjustable according to the size of the pouch 60. Adjusting the size of the pouch can also change the level at which the weight of the belt is supported. A fastener material 36, such as Velcro™, is provided on the pouch assembly 30. Fastener material 36 is secured to the main pocket panel 32. Corresponding fastener material 38 is attached to the distal end of the lower flap 34. Fastener material 36 has a substantial height as compared to the height of fastener material 38, thus allowing the fastener material 38 to be secured to any suitable location along the height of the relatively larger panel 36. This adjustability allows the user to change the size of the pocket as needed according to the size of the pouch and the desired level at which the weight of the belt is supported.

A secondary or support plate pocket 45 is formed at the base location 22 on the inside of the ostomy support belt 20. The secondary pocket 40 is formed by an inner panel 42 attached to the inside of the belt 24 at the base location 22. The panel 42 and the base location 22 define concentric and substantially similar diametrical inner edges 40 of fabric material. Inner edges 40 are intended to be placed in concentric alignment with the stoma of the ostomate. The panel 42 forms an opening 45 (FIG. 1) in which a support plate 90 is installed to provide lateral support to the skin and tissue surrounding the stoma.

Figure 8:
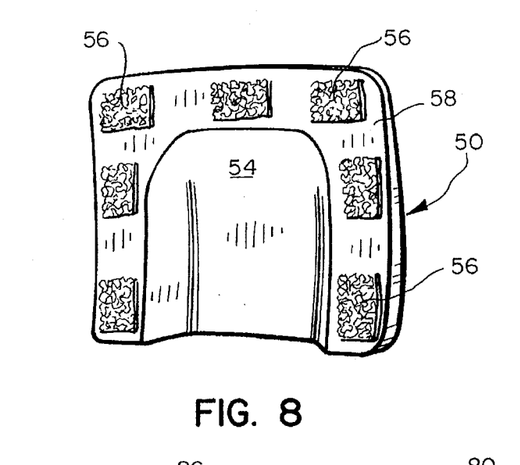
FIG. 8 is a rear perspective view of the guard of FIG. 7.

The base location 22 includes an outward facing panel 44 which defines the aperture 40. Fastener material 46, such as Velcro™, is secured to panel 44. Fastener material 46 provides areas to which a protective guard 50 may be secured. The protective guard 50 preferably comprises an outer rigid shell 52 which extends over and covers the stoma area to protect the stoma from irritation or blunt trauma, which is often caused by activities of a normal lifestyle and is even more likely to result from activities of an active lifestyle. The guard 50 includes a recessed portion 54 (FIG. 8) which forms a rigid protective umbrella for extending over and protecting the stoma. Although a preferred embodiment of the guard is shown to be rigid, it is to be understood that other types of protective guards, such as an inflatable guard or another type of guards, could be used without departing from the scope of the present invention. The guard 50 includes a suitable fastening material 56, such as Velcro™, for securing the guard 50 to the fastening material 46 on the main panel 44 of the base location 22.

FIG. 1 shows one type of a conventional pouch 60 for which the present ostomy support belt is intended to be used. The pouch 60 includes an attachment end 62 having a plurality of flanges to which conventional support devices and belts may be attached. The attachment end 62 extends through the apertures defined by annular edges 40 (FIG. 1) at the base location 22 of the ostomy support belt. The attachment end is secured in a conventional manner to a conventional adhesive pad 70 (FIG. 1). The adhesive pad includes an aperture 72 sized to correspond to the size of the stoma of a particular patient. A tapered wall 74 is designed to conform to the particular ostomate's abdominal wall so that the stoma can extend through aperture 72. Conventional flat pads may also be used without departing from the scope of the present invention. Adhesive material (not shown in FIG. 1) secures the pad to the skin surrounding the stoma. It is also to be understood that one or two piece pouches may be used in connection with the present invention.

The conventional pouch 60 includes a main containment structure 64, which preferably is made of plastic material. An end opening 66 is provided so that the contents of the containment structure 64 may be emptied periodically. A conventional clip or other suitable fastener 68 secures the end opening 66 in a closed position when the pouch is properly secured to the adhesive pad 70. The end section 62 seals together with the attachment location on the adhesive pad in a conventional manner to prevent any leakage from occurring between the two structures.

A resilient, semi-rigid support plate 90 is preferably placed within the pocket 45 formed at the base location 22 on the inside of the ostomy support belt 20. The support plate includes an aperture 92 through which the pouch 60 extends. The support plate 90 is designed to provide peripheral and lateral support to the areas of the skin and tissue surrounding the stoma. This additional lateral support also maintains the adhesion between the adhesive pad 70 and the skin surrounding the stoma so that leakage does not occur. Further, the additional lateral support provided by plate 90 will reduce mounding around the stoma and will reduce skin irritation normally associated with supporting the substantial weight of the pouch by the skin surrounding the stoma.

Figure 4:
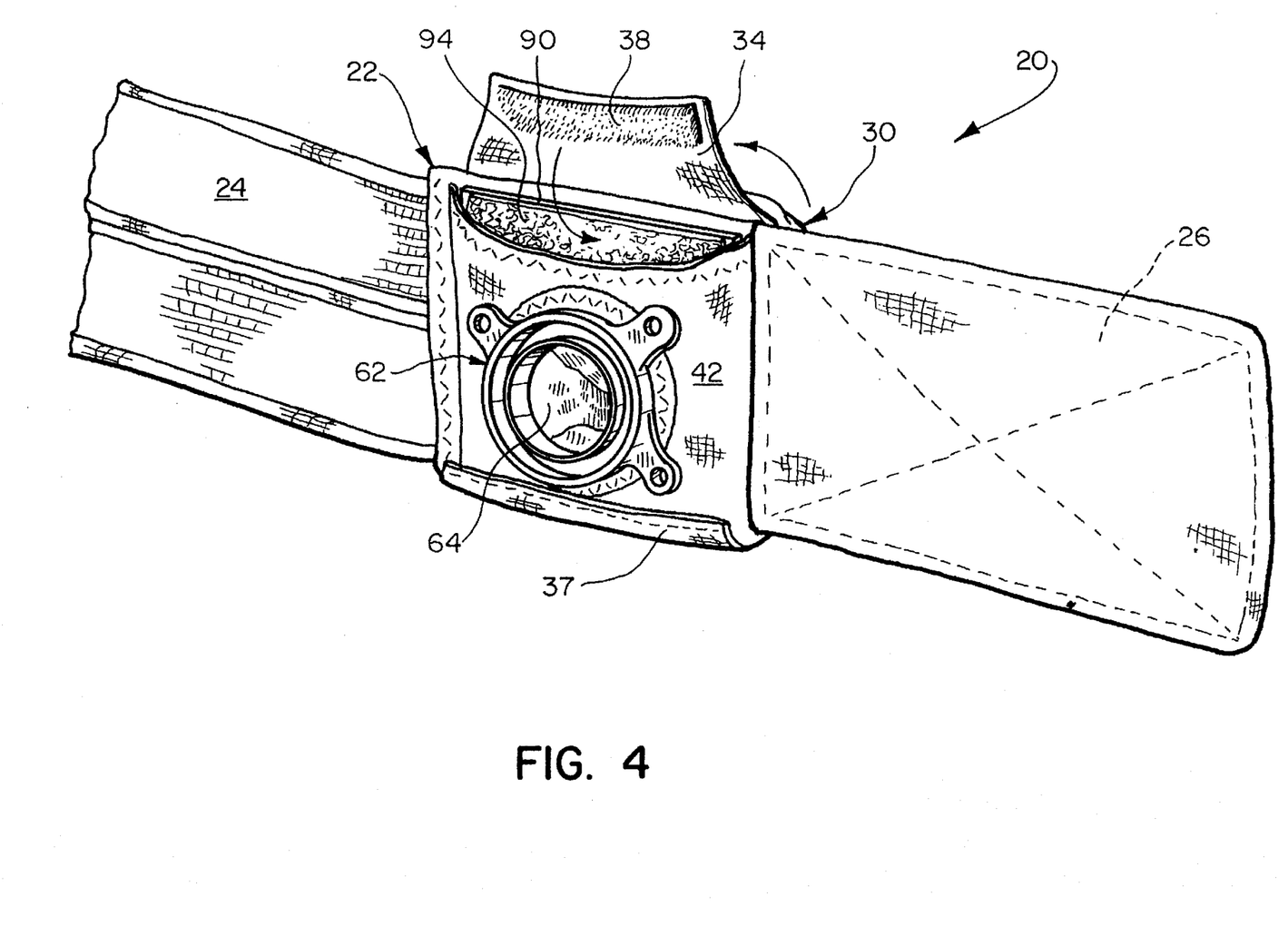
FIG. 4 is a rear perspective view, partly in section, of the ostomy support belt of FIG. 1 with the primary pouch of the belt shown in a hide-away position at the belt location.
Figure 5:
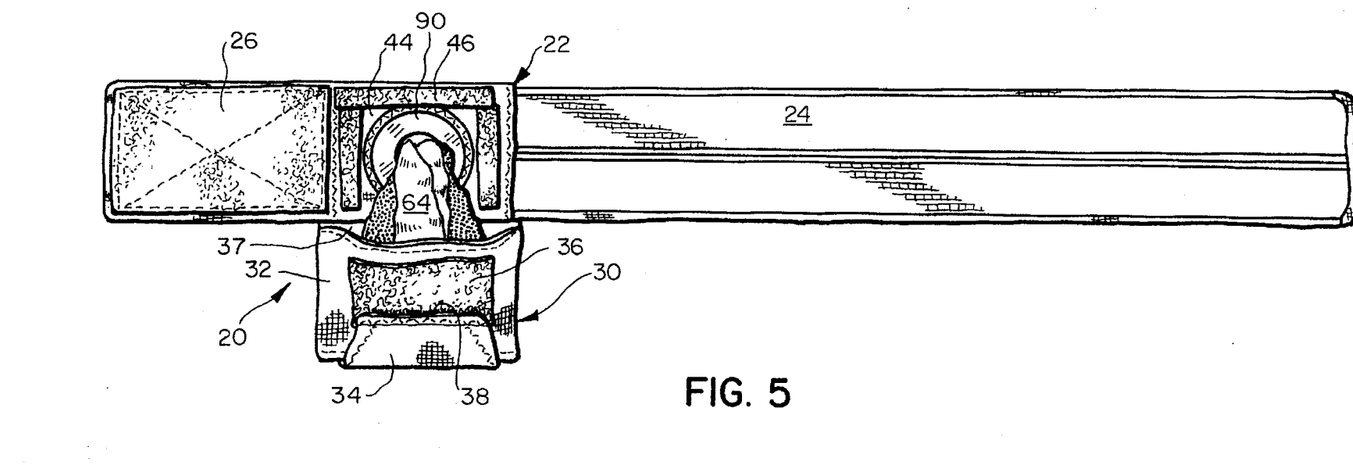
FIG. 5 is a front elevation view of the ostomy support belt of FIG. 1 including a conventional pouch held within and supported by a main pocket of the support belt.
Figure 6:
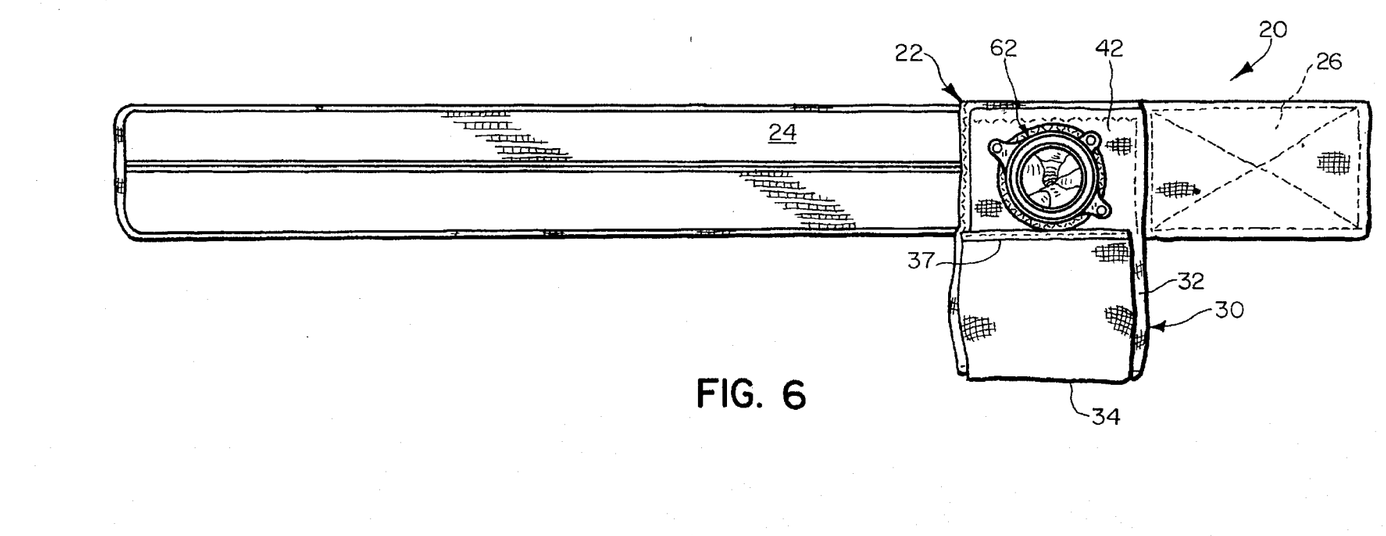
FIG. 6 is a rear elevation view of the ostomy support belt, including the pouch, as shown in FIG. 5.
Figure 11:
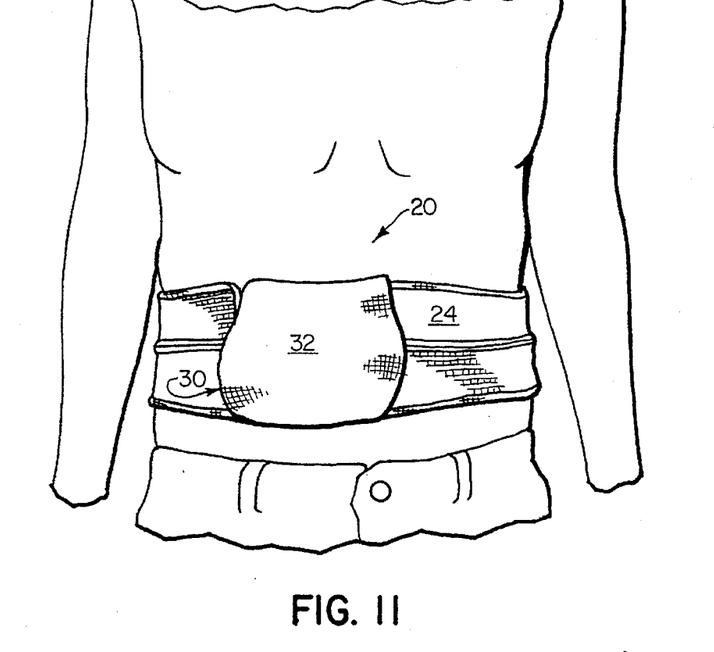
FIG. 11 is a partial front view of the ostomy support belt of FIG. 1 secured about the abdominal region of an ostomate with the main pocket folded in a hide-away position at the belt level.
Figure 12:
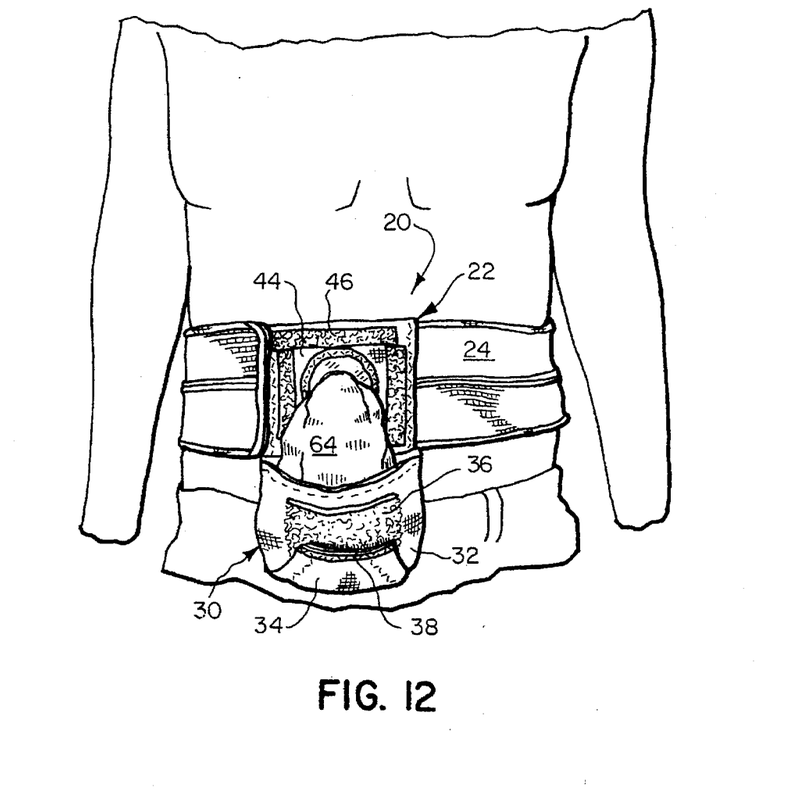
FIG. 12 is a partial front view of the ostomy support belt of FIG. 1 secured about the abdominal region of an ostomate with the main pocket extending down in a normal position supporting the pouch.

An other advantageous feature of the ostomy support belt of the present invention is shown in FIGS. 4 and 11–12. The main pocket 30 of the ostomy support belt is attached to and extends below the belt line during normal wearing. Under certain circumstances, such as without limitation during intimate relations or sports participation, the combined pouch 60 and pocket 30 may swing about back and forth as a pendulum which can be distracting and adversely affect the activity in which the ostomate is engaged. The present invention provides a particularly advantageous hide-away feature to disable the pendulum-like effects of the pouch 60. The main pocket 30 and pouch 60, being emptied first, are folded about extension piece 37 in a position securely against the ostomate's stomach at a location corresponding to the belt area. To place the belt in the hide-away position, the lower flap 34 is removed from its secured position to the main pocket panel 32 by separating the attachment devices 36 and 38. Thereafter, as shown in FIG. 4, the main pocket 30 and the pouch 60 are pivoted upwardly about attachment flap 37 and the flap 34 is attached to a fastener material, such as a Velcro™, mounted to the support plate 90. The end flap 34 holds the pocket 30 and the pouch 64 in a relatively unnoticeable position against the belt worn by the ostomate. The hide-away position eliminates the pendulum-like movements that usually result when the main pocket 30 and pouch 60 are in the normal position.

Figure 7:
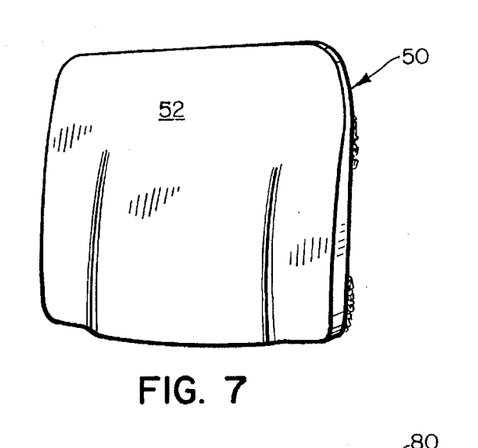
FIG. 7 is a front perspective view of a preferred embodiment of a guard securable to the front side of the ostomy support belt as shown in FIG. 1.
Figure 9:
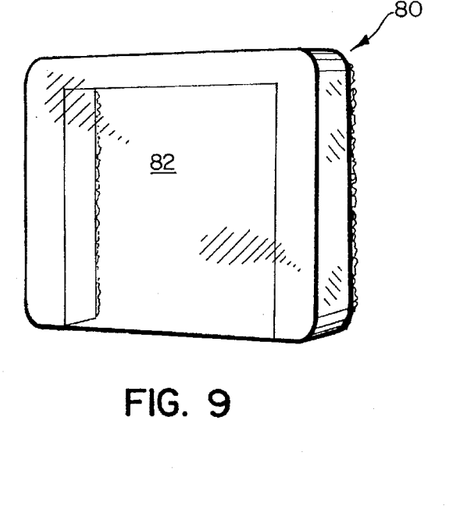
FIG. 9 is a front perspective view of a second preferred embodiment of a guard securable to the front side of the ostomy support belt shown in FIG. 1.
Figure 10:
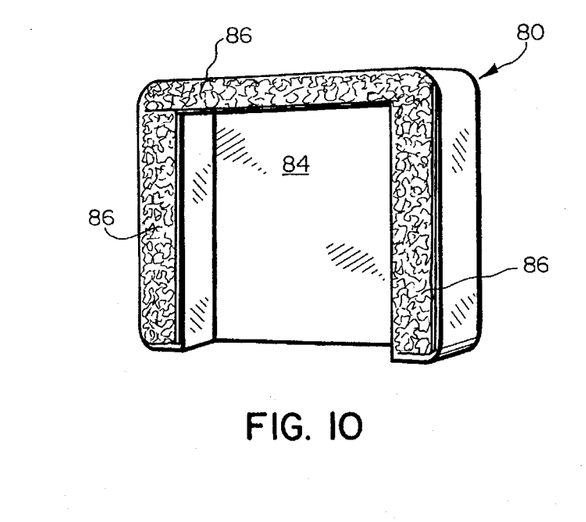
FIG. 10 is a rear perspective view of the guard of FIG. 9.

FIGS. 9 and 10 show an alternative embodiment of a guard 80 securable to the attachment sections 46 of the base location 22. The guard 80 includes an outer rigid surface 82, and an inner concave area 84 positioned to correspond with the stoma area. Attachment surfaces 86 correspond with attachment surfaces 46 (FIG. 1) of the panel 44 for attaching the guard 80 to the base location 22 of the ostomy support belt. This embodiment offers similar advantages as compared to the embodiment shown in FIGS. 7 and 8, only with a different shape and profile.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications with the proper scope of the appended claims appropriately interpreted in accordance with the doctrine of equivalents.

I claim:

1. An ostomy support belt, comprising:

a belt having a length sufficient to extend around an ostomate's waist;

an aperture formed in the belt at a base location, the aperture positioned so that it is capable of corresponding to a stoma of the ostomate, the aperture sized to allow insertion of a pouch for holding bodily drainages;

a main pocket having a size coupled to the belt proximate the aperture to hold and support the pouch, the main pocket having sides and an adjustable bottom wall, the main pocket being independent from the belt, the bottom wall being repositionable relative to the sides to vary the size of the main pocket.

2. An ostomy support belt according to claim 1 wherein the belt includes a bottom edge, the main pocket being secured to the bottom edge of the belt and extending downwardly from the belt to provide a support location below the belt.

3. An ostomy support belt according to claim 1 further comprising a guard securable to the outside of the belt, the guard adapted to cover the stoma location to protect the stoma.

4. An ostomy support belt according to claim 1 wherein the belt includes an outside surface, and further comprising a rigid guard securable to the outside surface of the belt, the guard adapted to cover the stoma location to protect the stoma.

5. An ostomy support belt according to claim 1 wherein the belt includes an outside surface, and further comprising a guard securable to the outside surface of the belt, the guard forming a concave area which is positioned over the stoma to provide a rigid protective umbrella for the stoma.

6. An ostomy support belt according to claim 1 wherein the belt includes a lower edge, the main pocket being coupled to the lower edge of the belt, the main pocket extending downwardly from the belt.

7. An ostomy support belt according to claim 1 wherein the bottom wall of the main pocket is positionable at a particular height, the main pocket being adjustable to vary the height of the bottom wall.

8. An ostomy support belt according to claim 1 wherein the main pocket comprises a main pocket panel forming side walls of the main pocket and a hinged flap having a free edge, the free edge being attachable to the main pocket panel such that the hinged flap forms a bottom wall of the main pocket.

9. An ostomy support belt according to claim 1 wherein the main pocket comprises a main pocket panel forming side walls of the main pocket and a hinged flap having a free edge, the free edge being attachable to the main pocket panel such that the hinged flap forms a bottom wall of the main pocket, the hinged flap being securable to various locations of the main pocket panel to form a variably sized main pocket.

10. An ostomy support belt according to claim 1, further comprising:

a secondary pocket formed in the belt at the base location;

a support plate positioned inside the secondary pocket, the support plate having a support plate aperture appropriately sized according to the ostomate's stoma, the support plate providing lateral support to an area surrounding the stoma when the ostomy support belt is worn by the ostomate.

11. An ostomy support belt according to claim 1 wherein the main pocket comprises a surrounding wall section, an open top end, and the bottom wall being hinged, the hinged bottom wall being securable to a portion of the surrounding wall section.

12. An ostomy support belt according to claim 1 wherein the main pocket comprises a surrounding wall section, an open top end, and the bottom wall being hinged, the hinged bottom wall being securable to the surrounding wall.

13. An ostomy support belt, comprising:
   a belt having a length sufficient to extend around an ostomate's waist;
   an aperture formed in the belt at a base location, the aperture positioned so that it is capable of corresponding to a stoma of the ostomate, the aperture sized to allow insertion of a pouch for holding bodily drainages;
   a rigid guard attachable to the belt to cover the base location, the rigid guard forming an opening when attached to the belt through which the pouch extends, the rigid guard protecting the stoma from damage.

14. An ostomy support belt according to claim 13 wherein the guard forms a concave area which is adapted to be positioned over the stoma to provide a rigid protective umbrella for the stoma.

15. An ostomy support belt for use with a pouch for holding and containing bodily drainages, comprising:
   a belt sized to extend around an ostomate's waist, the belt having an inner side and an outer side;
   a belt aperture formed in the belt at a location capable of corresponding to a stoma of the ostomate, the aperture providing a location through which a pouch for holding bodily drainages extends;
   an inner pocket formed on the inner side of the belt, the inner pocket having an inner pocket aperture corresponding in size to the belt aperture;
   a support plate independent and separate from the pouch, the support plate being positioned inside the inner pocket, the support plate having a support plate aperture for surrounding the stoma, the support plate providing lateral support to areas surrounding the stoma.

16. An ostomy support belt according to claim 15 wherein the support plate is semi-rigid and adapted to conform to an abdominal region of the ostomate and provide lateral support to areas surrounding the stoma.

* * * * *